(12) United States Patent
Collister

(10) Patent No.: US 6,459,995 B1
(45) Date of Patent: Oct. 1, 2002

(54) ELECTRICAL MEASUREMENT OF OIL QUALITY

(75) Inventor: Christopher John Collister, Stowell (GB)

(73) Assignee: Lubrigard Limited, Exeter (DE)

( * ) Notice: Subject to any disclaimer, the term of this patent is extended or adjusted under 35 U.S.C. 154(b) by 0 days.

(21) Appl. No.: 09/423,478

(22) PCT Filed: May 7, 1998

(86) PCT No.: PCT/GB98/01321

§ 371 (c)(1),
(2), (4) Date: May 4, 2000

(87) PCT Pub. No.: WO98/50790

PCT Pub. Date: Nov. 12, 1998

(30) Foreign Application Priority Data

May 7, 1997 (GB) ................................................ 9709290

(51) Int. Cl.$^7$ .............................................. G01N 31/00
(52) U.S. Cl. .............................. 702/23; 702/24; 702/25; 702/104; 73/304 C; 73/64.41; 73/54.01
(58) Field of Search .............................. 702/23, 24, 25, 702/104; 73/304 C, 54.01, 54.02, 54.05, 61.44, 61.61, 61.43; 324/665, 670, 678, 689, 655, 668, 663, 682, 683, 675, 76.79, 662, 664, 671; 340/620, 439, 450.3, 618, 631

(56) References Cited

U.S. PATENT DOCUMENTS

| | | | |
|---|---|---|---|
| 4,064,455 A | | 12/1977 | Hopkins et al. ............ 324/61 R |
| 4,646,070 A | | 2/1987 | Yasuhara et al. ............ 340/603 |
| 4,806,847 A | * | 2/1989 | Atherton et al. ............ 73/304 C |
| 5,225,783 A | * | 7/1993 | Suzuki et al. ............... 324/655 |
| 5,260,667 A | | 11/1993 | Garcia-Golding et al. .. 324/694 |
| 5,313,168 A | * | 5/1994 | Ogawa ....................... 324/663 |
| 5,414,368 A | * | 5/1995 | Ogawa et al. .............. 324/675 |
| 5,594,163 A | * | 1/1997 | Suzuki ....................... 73/61.44 |
| 5,642,098 A | * | 6/1997 | Santa Maria et al. ..... 73/304 C |
| 5,929,754 A | * | 7/1999 | Park et al. ................ 73/304 C |

FOREIGN PATENT DOCUMENTS

DE  195 17 390  11/1995
GB  2 306 660  5/1997

* cited by examiner

Primary Examiner—John S. Hilten
Assistant Examiner—Hien Vo
(74) Attorney, Agent, or Firm—Marshall, Gerstein & Borun.

(57) ABSTRACT

Method and apparatus for measuring oil quality based on the permittivity of the oil comprising a capacitive or radiative sensor for exposure to the oil, and an oscillator circuit including the sensor, wherein the oscillator circuit comprises a LC or crystal oscillator which provides an output signal, the amplitude of which is dependent upon the lossiness of the Tan δ of the oil, and a measuring device that responds to the amplitude of the output signal as a measure of oil quality.

18 Claims, 12 Drawing Sheets

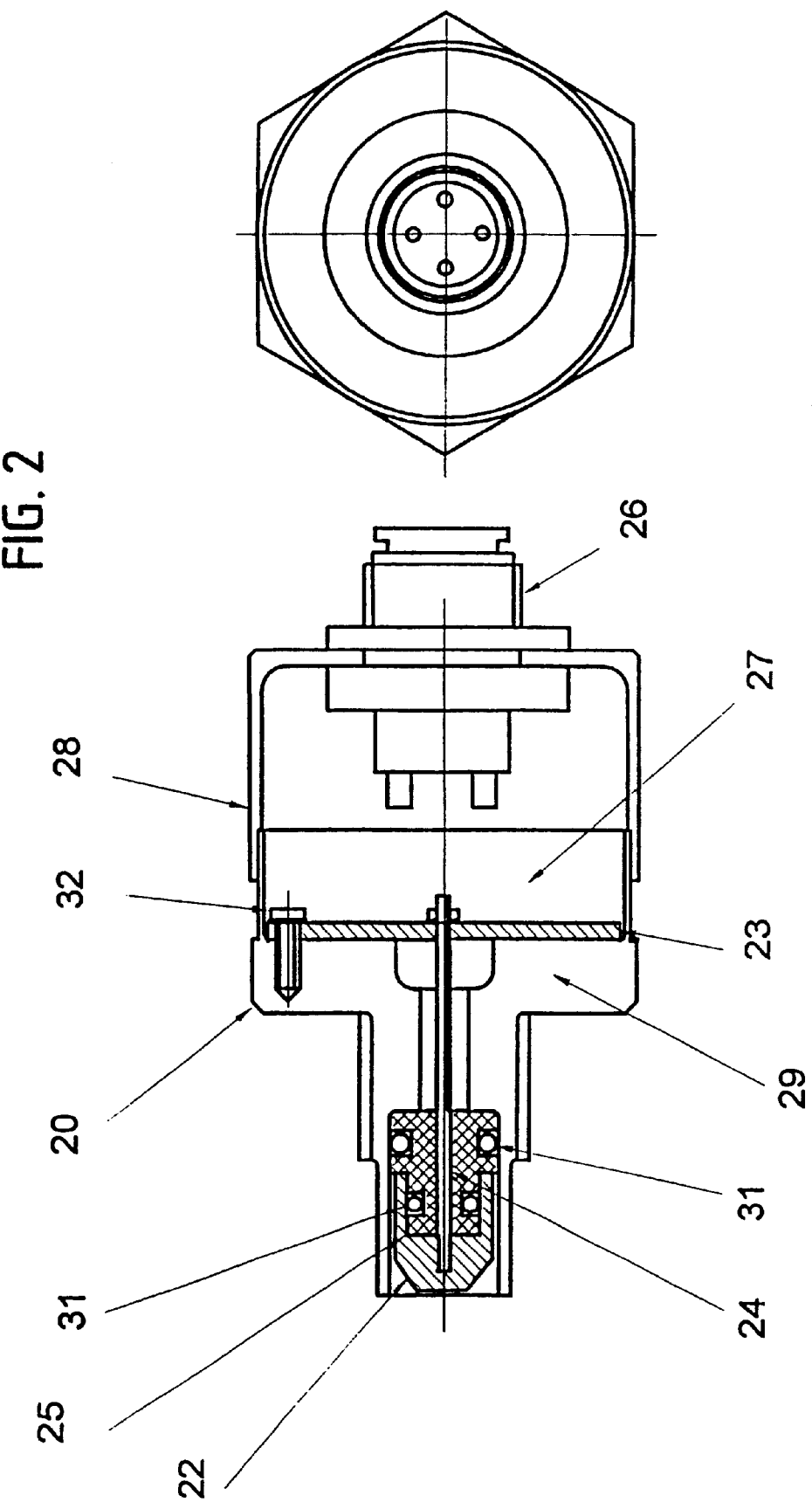

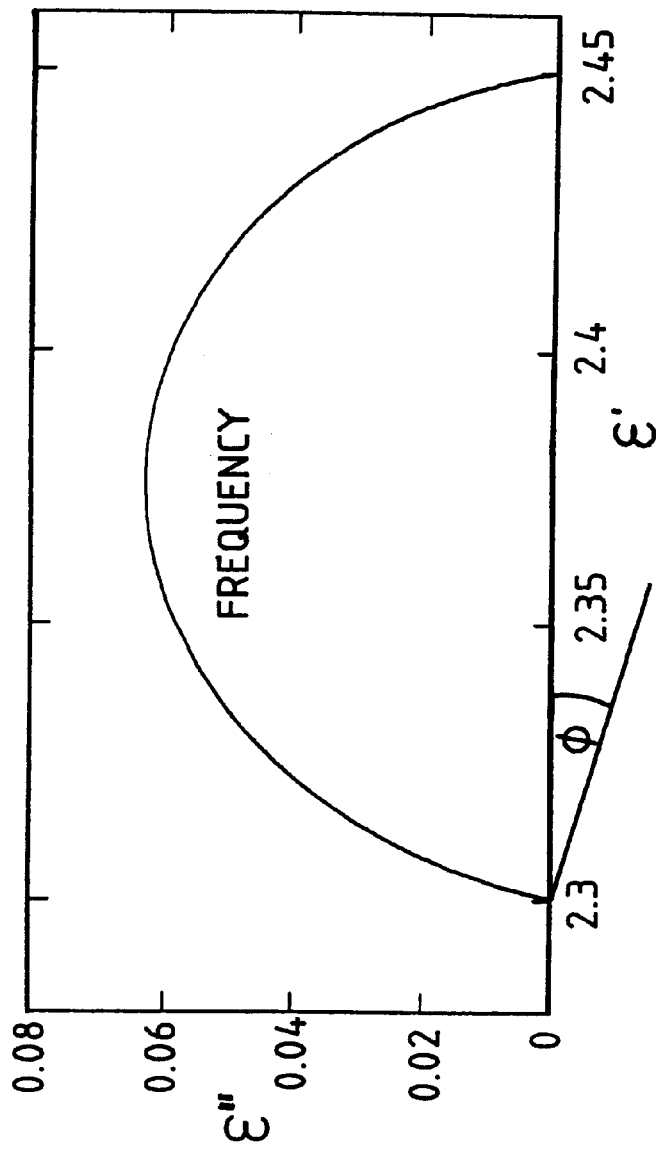

ELECTRICAL MEASUREMENT OF OIL QUALITY

Figure 1A:
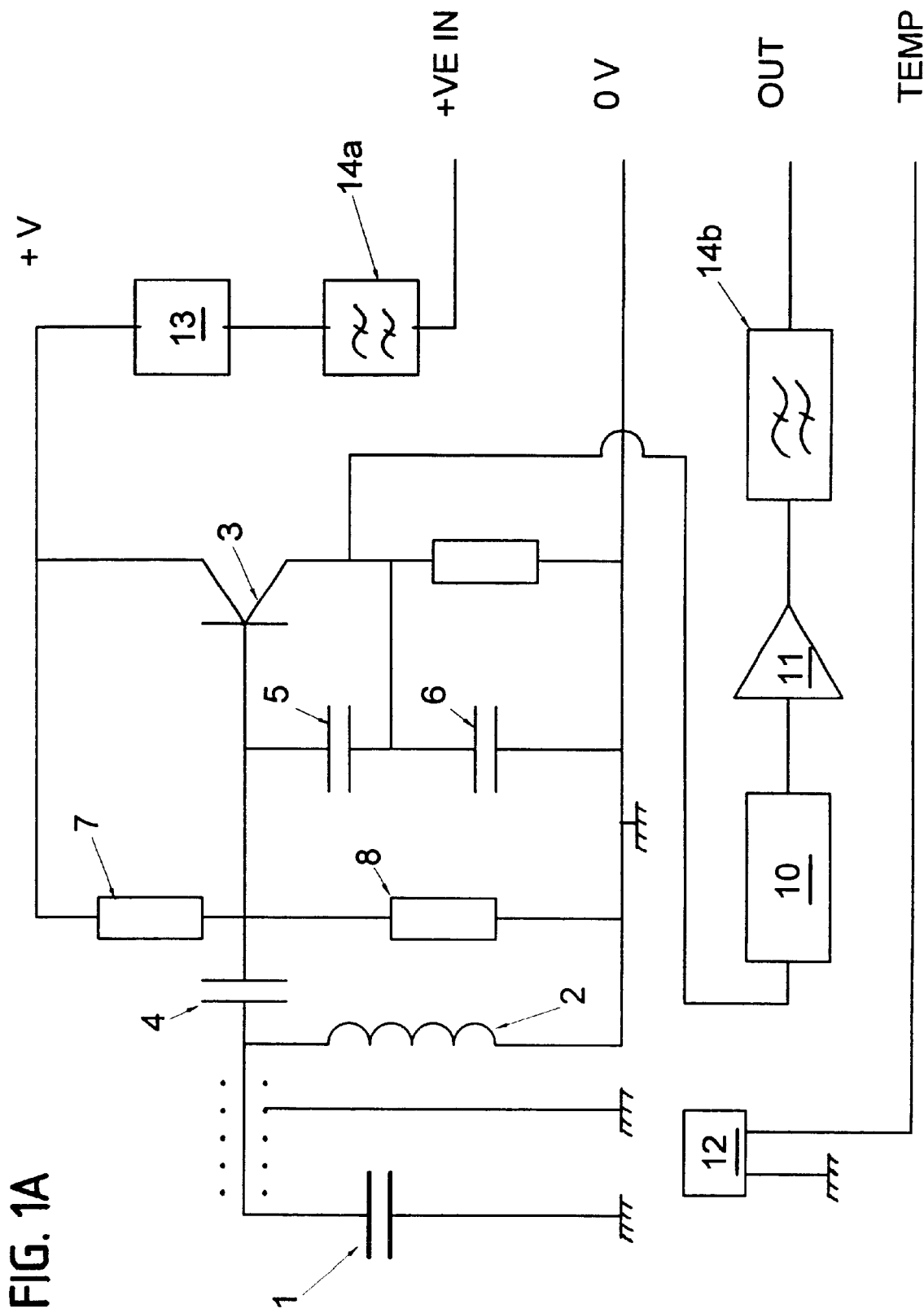

This invention relates to a method and apparatus for electrical measurement of oil quality, applicable to diesel fuel, or hydraulic, gearbox, transformer or engine oil, and preferably lubricating oil; and especially a method and apparatus for use in an engine, machine or filter.

BACKGROUND

It has been known for many years that the complex permittivity (or dielectric coefficient) of an engine lubricating oil changes with use, that is to say, both the real pan and the imaginary part change in response to changes in dissolved and suspended components of the oil. Such components are, for example, soot particles, water, acid combustion products, glycols, and ferrous and non ferrous metallic particles . In addition, oils often contain additives such as viscosity improvers and anti-oxidants which tend to break down with continued engine use, especially in the presence of water and metallic particles, which also accelerate the process of oxidation and general degradation.

It is also known that the reliability and longevity of an engine is crucially dependent upon the quality of its lubricating oil, and that an apparatus designed to detect some point at which the quality is deemed to be unacceptable would be desirable. In particular, when used in conjunction with a secondary bypass engine filter designed to remove particulate material down to 1 micron, such a device would be useful. Since such a filter may pass say 1% of the output from the oil pump, the differential pressure across the input and output of the filter is very low. making it difficult to measure. Consequently it is also difficult to know whether the filter element has become blocked. If this were to happen, however, the effect of the bypass filter in removing debris would be lost, and the concentration of contaminants would rise rapidly. Such a rise, or rate of change, could be detected by an oil quality monitor, enabling the filter or filter element to be replaced. If the oil quality monitor were to indicate poor quality, a sample may then be taken from the engine or machine, and sent to a suitable laboratory or facility for advanced spectrographic or chemical analysis, which may then reveal the presence of excessive soot, water, glycol, oxidation products, or metallic particles.

Also, degradation of most oils, such as due to oxidation or electrical breakdown, tends to result in the generation of products whose molecules are generally more polar than the oil from which they came. The base oil often comprises large hydrocarbon molecules which are generally only weakly polar, so the presence of most contaminants will result in an increase in one or both parts of the oil's complex permittivity. An oil quality monitor which measures permittivity is therefore suitable for measuring changes in, for example, transformer oil, or the oil in gearboxes and transmissions which may be subjected to the high temperatures and agitation which are conducive to oxidation.

Transmission units and other hydraulic systems such as rams may also become contaminated with water as a result of working in wet or damp environments. Water will cause an increase in both parts of the oil's complex permittivity, and may therefore be detected by apparatus according to the invention.

Advanced oil analysis as carried out by an accredited laboratory subjects oil samples to a battery of tests, one of which is often a basic measurement of dielectric properties, often carried out by hand. An oil quality monitor according to the invention may be incorporated into an automated production line. The invention may be adapted so that a sensing head is provided at the end of a slender flexible rod suitable for insertion into the dipstick orifice of, an engine or machine to allow in situ measurement of oil quality in an engine or machine not otherwise fitted with an oil quality measuring device.

DESCRIPTION OF PRIOR ART

In U.S. Pat. No. 3,182,255, Hopkins et al. describe a device in which a bridge circuit is used to measure the AC impedance of one arm of the bridge, which contains a capacitive element whose capacitance changes with the dielectric strength (sic) of a drop of lubricating oil.

This device requires the physical removal of an oil sample from the vehicle, and makes no distinction as to whether the measured parameter is the real or the imaginary part of the permittivity. It can be shown that the impedance of a capacitor containing a dielectric depends, to first order, upon the real part, and to second order, upon the imaginary part, so that, even if no change occurs in the real part, there will nevertheless be a change in the modulus, or magnitude, of the permittivity, if there is a change in the lossiness of the dielectric, such as may occur through the presence of carbon particles. It is this magnitude which is usually referred to loosely as "dielectric constant". In another patent, U.S. Pat. No. 4,064,455, Hopkins et al. describe the use of an identical bridge circuit, but this time in conjunction with data storage and computational facilities.

In EP 0291363, Warenghem et al. describe a parallel plate capacitor, the capacitance of which varies with the concentration of carbon particles. In this document, capacitance is not defined as complex and is taken to refer to the modulus, or magnitude. No indication is given as to the means by which capacitance is actually measured.

In U.S. Pat. No. 4,733,556, Meitzler et al. describe a parallel plate capacitive sensor designed to fit between the engine block and the filter, where changes in the magnitude of capacitance are used to generate changes in the frequency of an associated oscillator. It is this change in frequency which is measured and subsequently compared, not with soot content of the oil, but with its viscosity. Although it is known that the complex permittivity of polar liquids will change with viscosity, it is also known that the viscosity will tend to increase with increasing soot concentration. This increase in viscosity is a macroscopic effect in the sense that a soot particle is many orders of magnitude larger than a molecule, and it is felt that measurement of dielectric constant is not a reliable indicator of viscosity in sooty oils.

In U.S. Pat. No. 4,345,202, Nagy et al. describe the use of microwaves in the range 8 to 12 GHz to measure soot content in engine oil, whereby nulls in the standing waves on a coaxial transmission line are located by means of a plurality of detectors arranged along the transmission line which is itself immersed in the sump of the engine In U.S. Pat. No. 5,134,381, Schmitz et al. describe the use of a concentric capacitive sensor along whose axis passes, a fuel/alcohol mixture. Measurement of the capacitance of the sensor then provides the means whereby the alcohol content of the fuel may be determined, given a priori knowledge of the water content also. It appears that the capacitive sensor is excited by an external oscillator with the intention of measuring the impedance of the sensor and possibly also an associated phase shift.

Many other known devices are concerned with the measurement of the relative permittivity of fluids or fluid-like materials other than engine oil, many of which are distinctly multiphase. For example, in U.S. Pat. No. 2,121,920 a means for measuring the mass and moisture content of tobacco is described in which a parallel plate capacitive test cell is placed in series with an inductance. The resulting RLC circuit is tested for resonance by manually sweeping it with an oscillator, and measuring the magnitude and frequency of the response.

In U.S. Pat. No. 5,272,444, Cox describes a method for measuring the water content and salinity (water cut) of a petroleum stream via measurement of temperature, resistivity and dielectric constant, but gives no details as to the mechanical arrangement of the sensor. It is clear however that the sensor is excited by an oscillator running at one of two fixed frequencies viz. 15 MHz and 30 MHz.

In U.S. Pat. No. 4,932,243, Suh et al. describe an online means for measuring the moisture content of a material, for example polymer pellets, using a capacitive sensor comprising three conductive concentric cylinders through which the material passes axially. The capacitance and dielectric loss are determined using "well known techniques" which are not detailed.

In U.S. Pat. No. 4,288,741, Dechene et a). describe a method for measuring both displacement and conduction currents in a two phase fluid of which one is assumed to be conductive, to determine the relative fractions of the phase. This is achieved by driving a capacitive sensor via an oscillator of fixed frequency with the intention of separating the relatively large conduction current from the relatively small capacitive current due to the AC excitation voltage.

In U.S. Pat. No. 4,181,881, Preikschat describes an apparatus also intended to measure the so-called dielectric coefficient and conductivity of various materials. This appears to be a batch testing method, and precise details of the capacitive sensor are not provided, other than to describe it as an earthed rectangular box with an active centre electrode. The capacitive sensor is excited by means of a stable crystal oscillator, the bridge circuitry being designed to measure the phase and amplitude of the voltage across the sensor.

In U.S. Pat. No. 3,979,581, Reulend describes a method of measuring the mass of tobacco by exciting a capacitive sensor with a signal from a swept external oscillator. In this arrangement a discriminator measures the frequency while a demodulator and differentiator locate the frequency and amplitude at which amplitude resonance occurs. Precise details of the capacitive sensor are not provided, but it appears to be a parallel plate capacitor of indeterminate size, possibly of the same order of magnitude as a cigarette.

In GB 2249636, McBrearty describes an inline dielectric sensor using a form of interdigitating capacitor to measure the dielectric coefficient and loss factor of molten polymers. This is accomplished by exciting the sensor with a sine wave generator. In the document, it is stated that a current to voltage converter and a lock-in amplifier are used to measure the amplitude and phase of the resultant alternating current.

WO 96/28742 describes an apparatus intended specifically for on-line monitoring of engine lubricating oils in diesel engines, and discusses the necessity or desirability of carrying out continuous monitoring of the oil. In this apparatus, the fundamental principal is that of measuring the dielectric coefficient of the oil, but in order to extract the greatest amount of information from the sample, the apparatus uses an arrangement of electromagnets to concentrate ferrous particles in the vicinity of a flat interdigitating capacitive sensor. Although the interdigitating capacitor is an interesting and useful configuration, the given formula relating capacitance to the dimensions of the capacitor refers to a parallel plate configuration, and so appears to be inaccurate in that context. The capacitor forms part of an oscillator circuit whose frequency varies with the dielectric coefficient of the oil. Since no inductor is present in the block diagram or in the text, it is assumed that the circuit is found to be self resonant as a result of parasitic inductances or the self inductance of the capacitive sensor. The inventors state that "the sensor element is charged by an oscillator circuit . . . using a monostable multivibrator to generate an output signal at a frequency corresponding to the sensor element capacitance". This can be taken to mean that the oscillator frequency is determined directly by the sensor capacitance, or that the frequency of the oscillator is adjusted until it coincides with the self resonant frequency of the sensor. In any event, the measurand is the frequency, so the parameter actually being measured is the magnitude of the dielectric coefficient (sometimes referred to as "dielectric constant").

It is known that a few devices have attempted to correlate oil quality with dielectric coefficient by measuring the capacitance of a capacitor with the oil as a dielectric. This has been achieved by measuring either the change in AC impedance or by measuring the change in frequency when connected in an LC resonant circuit. However, in these cases what is actually being measured is the magnitude of the capacitance, which changes slightly with the lossiness Tan $\delta$ of the dielectric, but also changes with dielectric constant. Such devices therefore have the disadvantages of being sensitive to oil base type, and only being sensitive to the second order as regards the loss term Tan $\delta$.

SUMMARY OF THE INVENTION

The present invention provides apparatus for measuring oil quality based on the permittivity (dielectric coefficient) of the oil comprising a capacitive sensor for exposure to the oil, and an oscillator circuit including the sensor, characterised in that the oscillator circuit comprises an LC or crystal oscillator and provides an output signal, the amplitude of which is dependent upon the lossiness Tan $\delta$ of the oil, and measuring means that responds to the amplitude of said output signal as a measure of oil quality.

In particular, the amplitude can be inversely proportional to the Tan $\delta$ value. Tan $\delta$ is the ratio $e\ \epsilon''/\epsilon'$ where $\epsilon''$ is the imaginary part of the complex relative permittivity and $\epsilon'$ is the real part. The oil can be diesel fuel or another light mineral oil. The oil is preferably lubricating oil.

Thus, the output of the oscillator varies in response to changes in the lossiness of the dielectric medium (the oil), which in turn are determined principally by changes in the oil's soot content, acidity, and polar oxidation products. It is this change in the amplitude of the oscillator output which provides a measure of the oil quality.

The present invention is applicable to diesel fuel and oil in engines, or oil in hydraulic transmissions or machines, or oil in electrical machines where contaminants may be introduced into the oil by electrical breakdown or ingress of moisture.

The present invention also relates to an engine or machine including said electrical measuring apparatus. In particular, the sensor may be fitted to the oil supply tunnel or sump of the engine or machine. Alternatively, the sensor may be fitted to an oil filter, such as an oil bypass filter, attached to the engine.

The present invention also relates to an oil bypass filter for attachment to an engine, the oil bypass filter including said electrical measurement apparatus.

The present invention also relates to a method of measuring oil quality based on the permittivity of the oil using an oscillator circuit including a capacitive sensor, characterised in that the sensor is an LC or crystal oscillator which provides an output signal, the amplitude of which is dependent upon the lossiness Tan δ of the oil, and is used to give a measure of oil quality.

The sensor is preferably incorporated in a sensor head which is generally concentric or radially symmetric. It is preferably perforated or slotted to allow the free passage of oil over the electrically active surfaces of the sensor. Typically, the sensor head is about 10 mm in diameter, being small enough to fit into a hole such as might be provided in an engine for an oil pressure switch, such as a ⅛" NPT (National Pipe Thread) or ¼" BSP (British Standard Pipe) orifice. The associated oscillator electronics are located in the space behind the sensor head, which can take the form of a hollow hexagonal nut approximately 30 mm A/F by 20 mm deep. Since the electronic circuitry is at approximately the same temperature as the oil, it comprises components which will operate in elevated temperatures, for example, up to 150° C., and, optionally, which will also provide compensation to allow for temperature dependent changes in the dielectric medium.

It is known that changes in temperature affect electronic components such as transistors, inductors and capacitors, so that the output of the circuit, independently of the oil dielectric, is a function of temperature. The electrical properties of the oil itself are also affected by temperature. The most visible effect is the change in density, which is effectively linear over the range of interest, that is, from about 30° C. to 150° C. It follows that the concentration of contaminants, being inversely proportional to volume, will fall with increasing temperature. Simultaneously, however, the viscosity of the oil also falls with temperature, allowing greater freedom of motion for the constituent molecules, and it can be shown theoretically that the greater the average dipole moment of the liquid, the greater will be its dependence on temperature. In order to operate accurately over a wide range of temperatures, some form of compensation is necessary. Incorporated into the electronics is a small temperature sensor whose output, after suitable buffering, is passed out of the sensor head to a display unit.

The display unit incorporates a microprocessor which accepts as input the output voltage from the oscillator and the output from the temperature sensor. By means of a suitable lookup table or algorithm, this allows the appropriate adjustments to be made in order to render the final indication independent of temperature over the range say 30° C. to 150° C.

Figure 9:
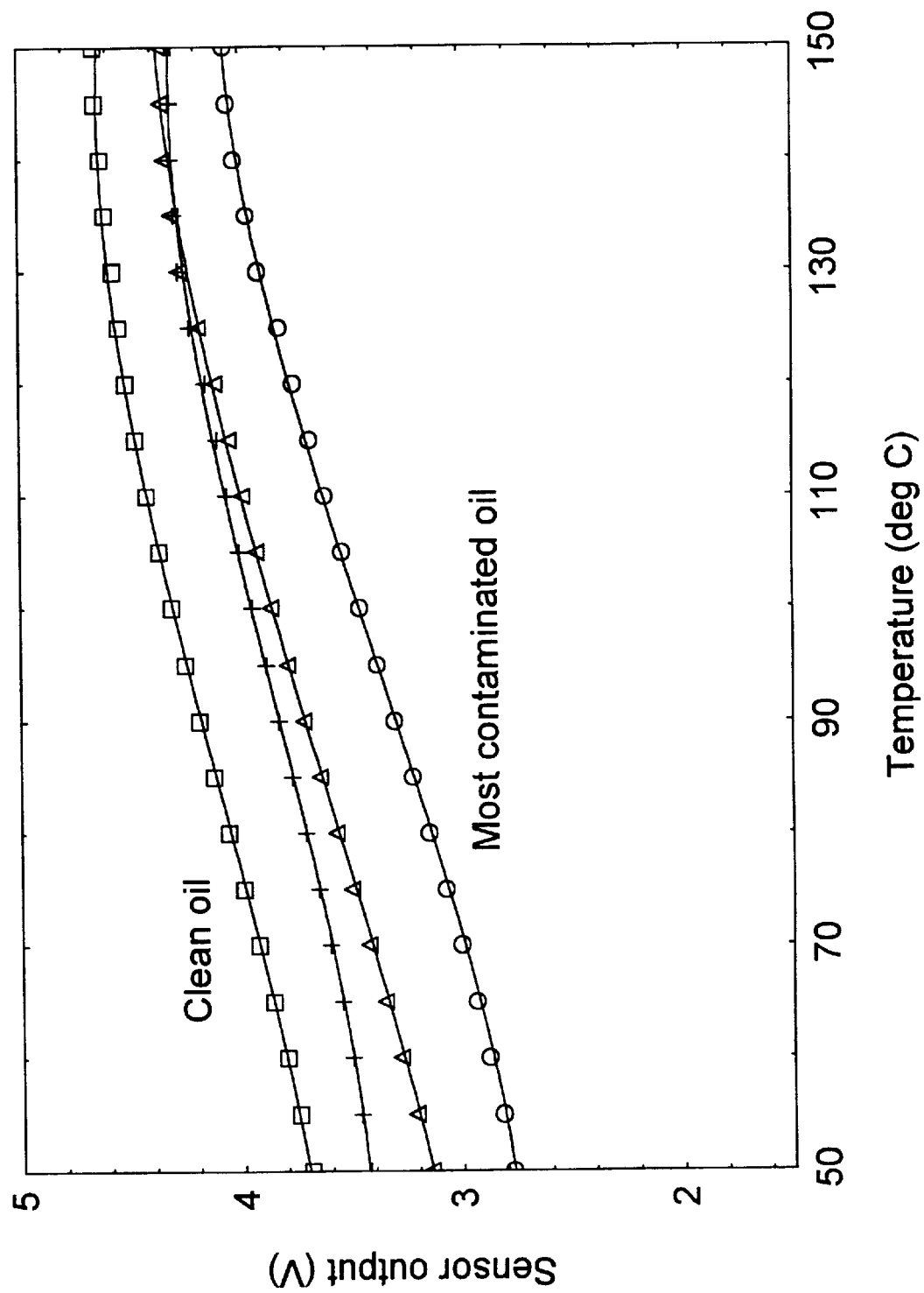

Generally, the curve showing oscillator output versus temperature is a bivariate function of permittivity and temperature, so full compensation requires a two dimensional lookup table or algorithm. However, it is found in practice that with the correct choice of operating frequency the slope of the curve is only weakly dependent on the concentration of contaminants, allowing the use of a simpler one dimensional table. FIG. 9 shows a number of typical curves where the change in oscillator output is plotted against temperature. The upper curve is for a clean engine oil, while the lower curves are for progressively more contaminated engine oil.

Figure 10:
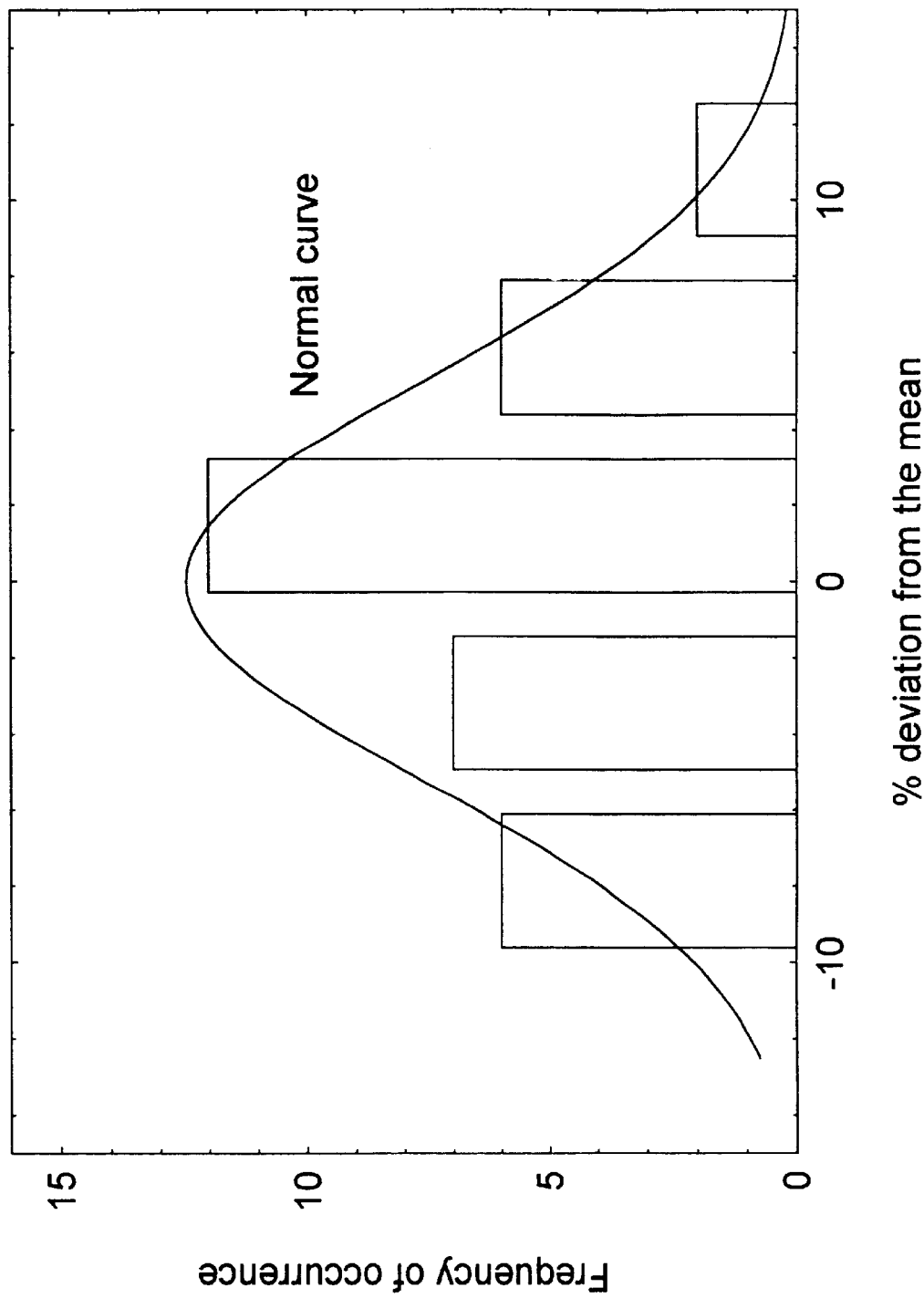

Oils are generally a complex mixture of hydrocarbons and proprietary additives, such that the output of the oscillator differs slightly according to the precise formulation. Although it has been found in practice, that the output differs by only a few percent to within one standard deviation over a wide range of different oils from different manufacturers (as shown in FIG. 10), calibration means is included to eliminate even this small source of error. When the vehicle or machine is serviced or supplied with fresh oil, the microprocessor may accept an input from a recessed switch or coded transmitter when the correct operating temperature has been reached, such that that particular value is held in memory, and therefore becomes the baseline against which all subsequent readings will be compared.

In the event of the main power supply being cut, such as removal of the vehicle or machine's battery, the contents of the memory are retained in, for example, an electrically erasable programmable read only memory (EEPROM). This same EEPROM may also hold several hundred sets of readings sampled over the lifetime of the oil, typically 300 to 500 hours. The data may then be downloaded into a computer for subsequent examination and analysis, or it may be suitably encoded and transmitted to a remote location by radio for example. In addition to the measured value of the oil's quality, the rate of change of the device's output is an important indicator of engine health. If the slope of output versus time should unexpectedly increase, this would tend to indicate a sudden increase in contaminants, requiring immediate remedial attention before damage should occur. In order to improve the reliability of the data, the microprocessor accepts for example 10 measurements at short intervals, such that the final value displayed or stored is the arithmetic mean of the measured values.

The final, visible part of the microprocessor's output may take the form of a warning light or buzzer, or for test and diagnostic purposes may take the form of an alphanumeric display.

In the preferred sensor, the body of the sensor is at ground potential, while an integral automotive style connector provides one pin for the output signal, one pin for the temperature output, and a further pin for DC power input, which may be 12V or 24V.

In one embodiment, the apparatus is used in conjunction with a secondary filter. In this way, oil drain intervals may be extended with consequent cost savings, and the reliability of the engine is enhanced by the use of oil of consistently high quality. Additionally, analysis of the oil can provide an indication of faults in the engine allowing early rectification and the planned scheduling of preventive maintenance to avoid expensive downtime.

The preferred apparatus according to the present invention is, advantageously, of very low cost, for example, comparable with that of an inexpensive automotive pressure sensor, and of small size, and requiring little or no modification to the engine or machine. It is preferably intended to be fitted permanently to the engine or secondary filter, and to monitor the quality of the oil. continuously throughout the life of the engine or machine. It is preferably insensitive to changes in temperature, within a range of, say, 30° C. to 150° C., or in the case of hydraulic oils, from 20° C. to 100° C. It is insensitive to changes in base oil type from one manufacturer to another. In a preferred embodiment, the apparatus is powered directly by the engine or vehicle 12V or 24V electrical supply, and provides a single output consisting of an analogue voltage which varies in response to changes in the electrical properties of the oil. This signal may be used to drive a dashboard display which indicates the current state of the oil to the operator, and which may include a visible or, audible warning to indicate a filter change, oil change, or sample to be sent for analysis.

In a further embodiment, the output may be passed to the vehicle's on-board computer, where the data may be sampled periodically and stored in memory for real time analysis or for subsequent downloading and examination.

In a further embodiment the sensor comprises an oscillator running at, say, 200 to 300 MHz and mounted on a printed circuit board (PCB) approximately 8 mm wide by 20 mm long. This small size is achieved through the use of surface mount components. The active sensing head is attached directly to the PCB and surrounded by a perforated metallic cover which provides mechanical protection, electrical screening and a return path for radiated electromagnetic energy. A small temperature sensitive element such as a thermistor is also fitted, and its output carried along a flexible hollow tube such as the outer part of a Bowden cable. The oscillator is supplied with power from a separate regulated supply, which is also fed down the hollow tube. Careful choice of the bias point of the oscillator will ensure that, as the oscillator voltage varies with Tan $\delta$, so also does the current, which then reflects any change in Tan $\delta$ due to contamination of the oil. Temperature compensation is applied in the manner already referred to by measuring the output from the temperature sensor, and then applying a correction in the display unit. In a further embodiment, the output from the temperature sensor is digitised and carried on the power supply lead. An active sensor of this size may advantageously be used for attachment to the end of a vehicle's dipstick (normally used for checking oil levels), or it may form part of a separate instrument for use by garages and testing stations to carry out a quick check on oil quality for stationary vehicles or machines. The sensor may be used for measuring the quality of oil in an engine, hydraulic machine, gearbox, or any other apparatus using non polar mineral oils.

Figure 1B:
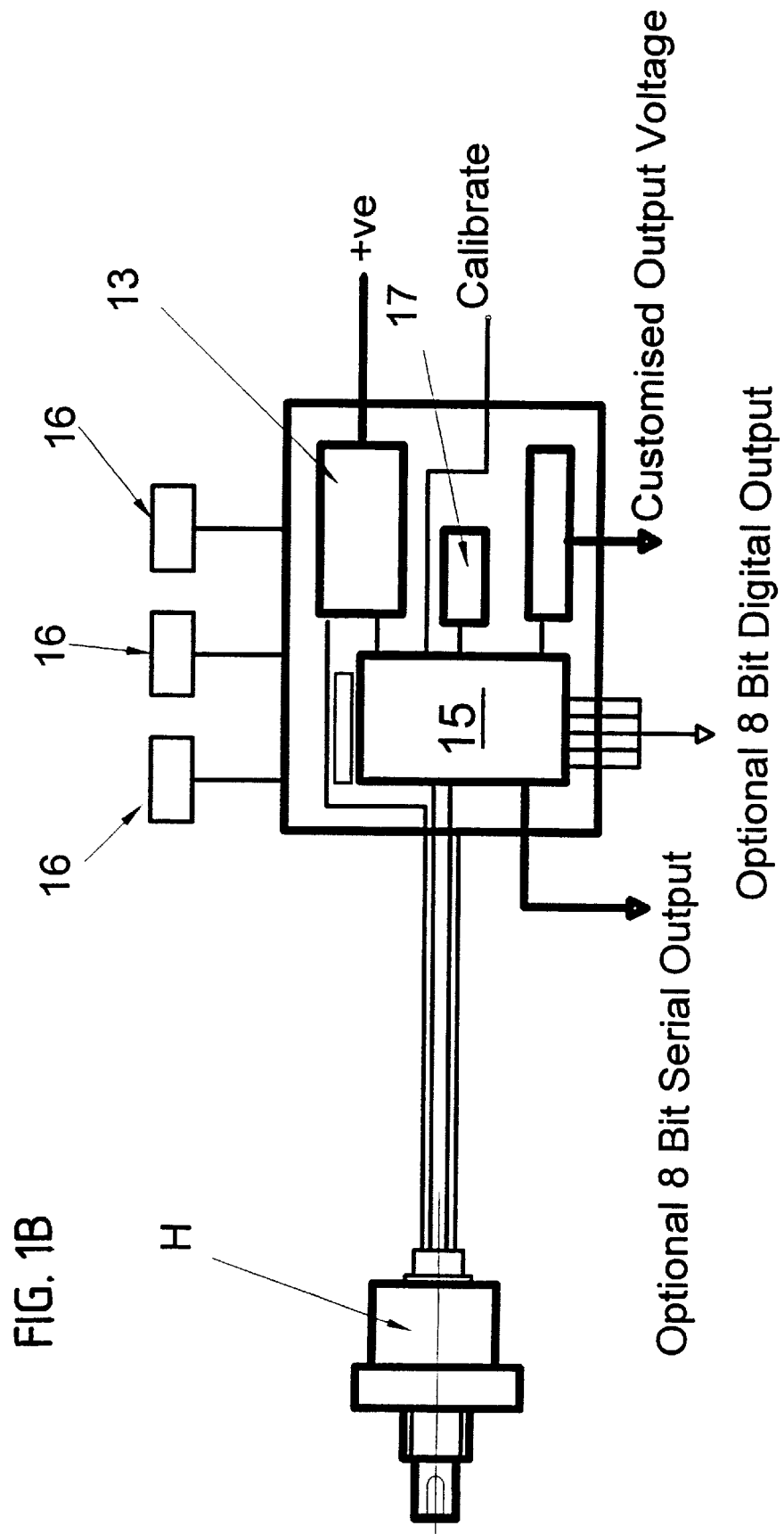
Figure 3:
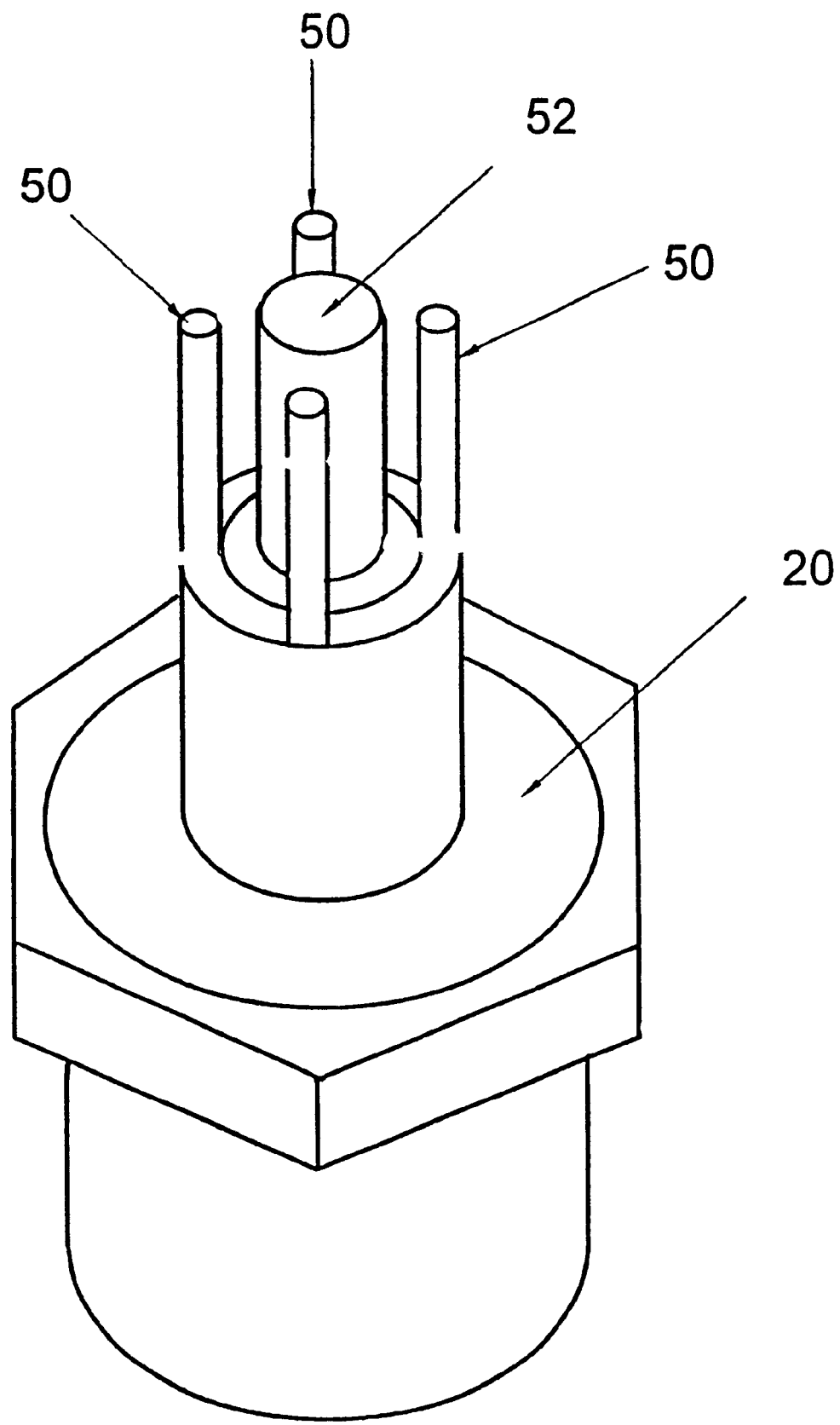
Figure 4A:
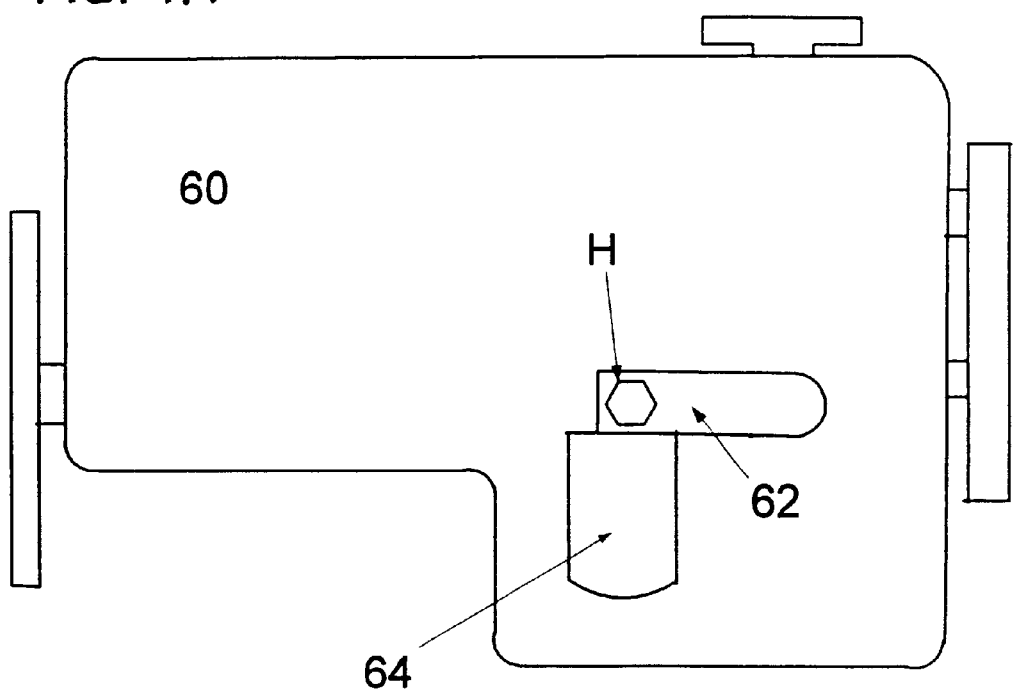
Figure 4B:
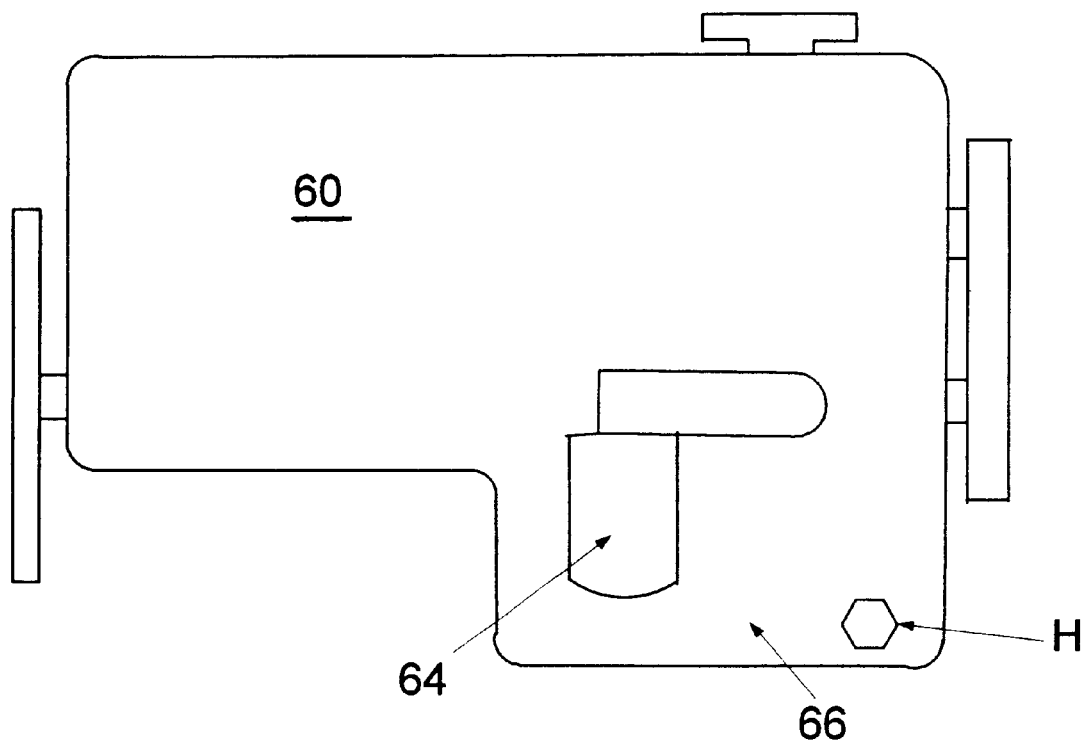
Figure 5:
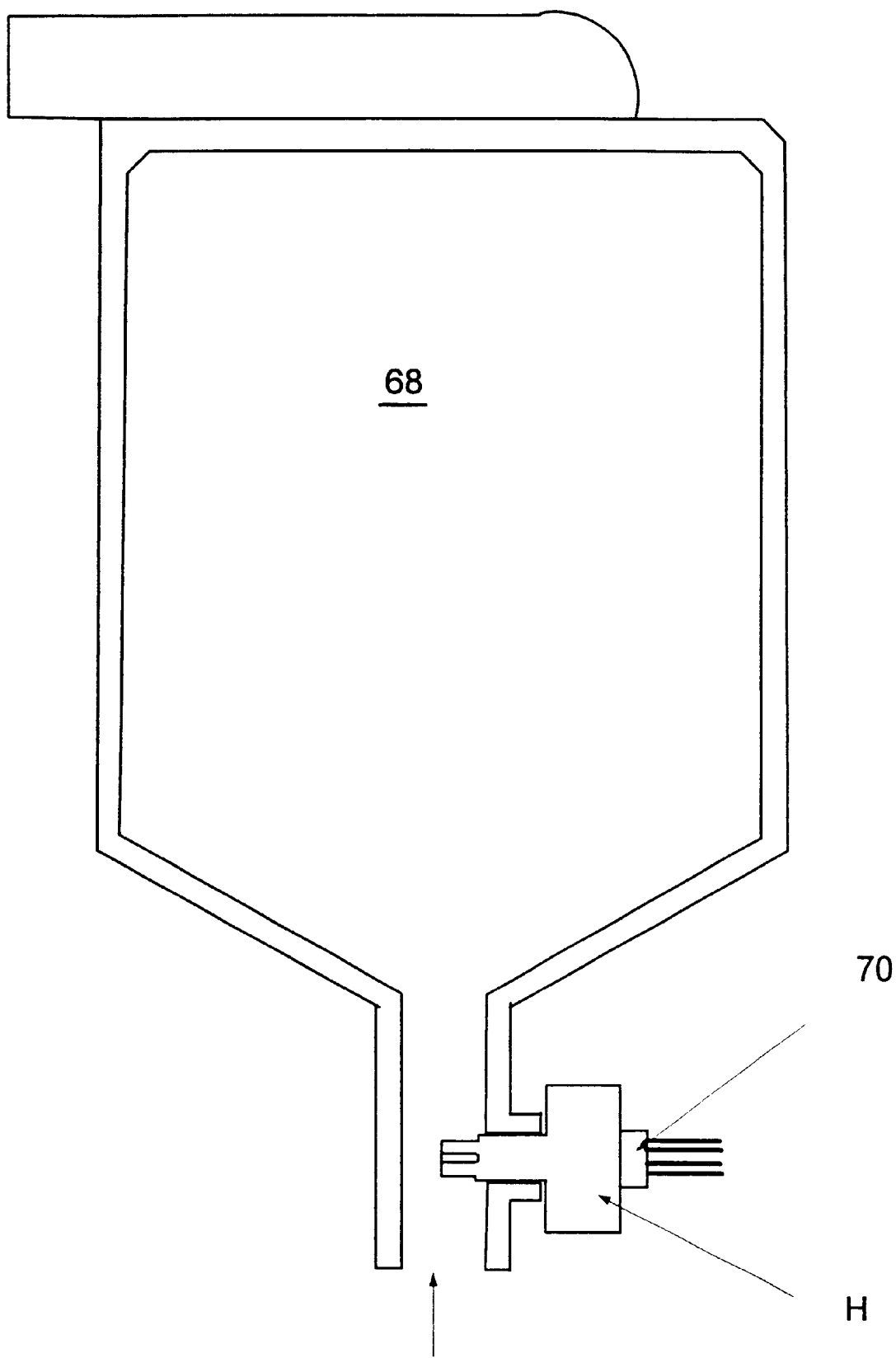
Figure 6:
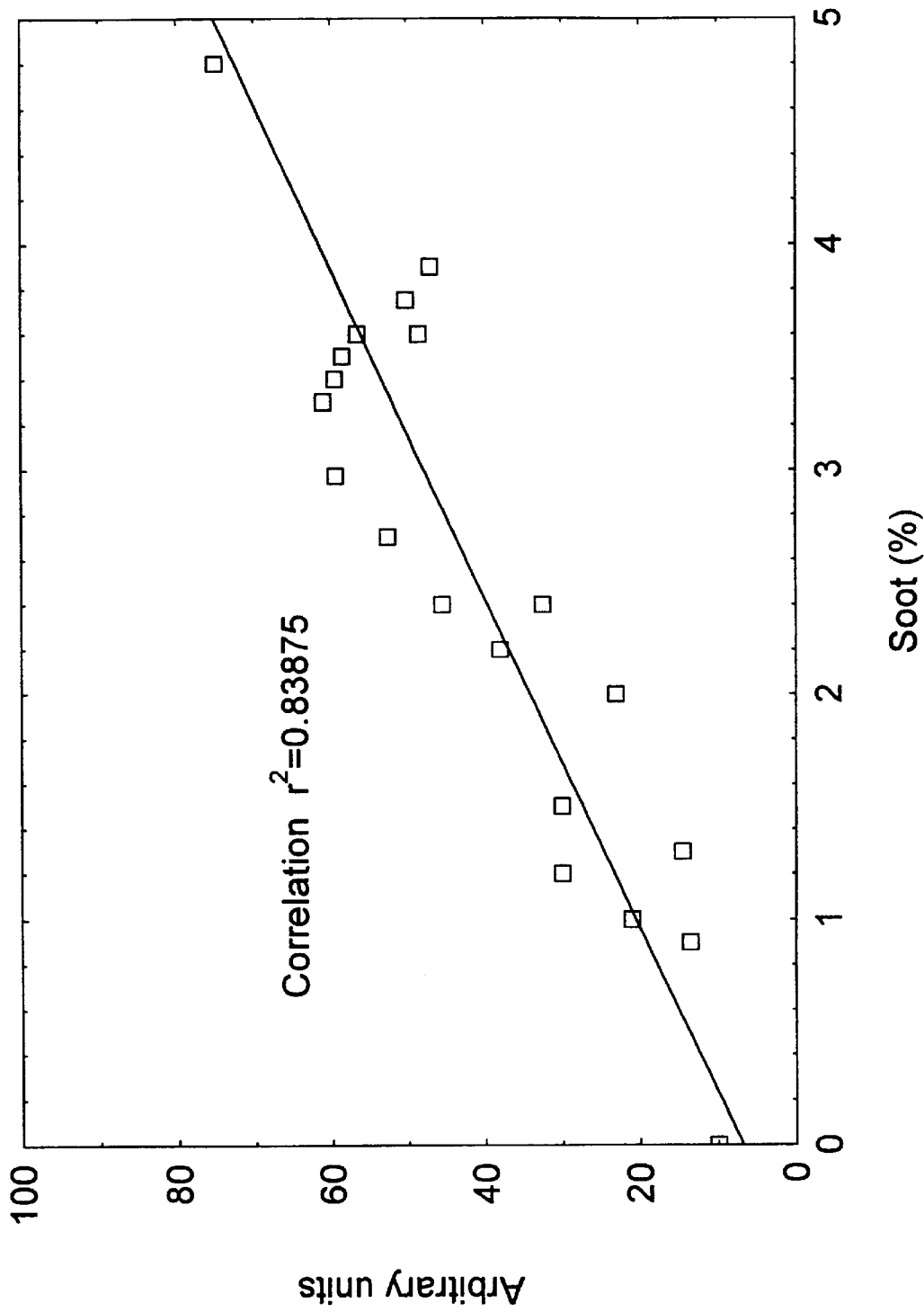
Figure 7:
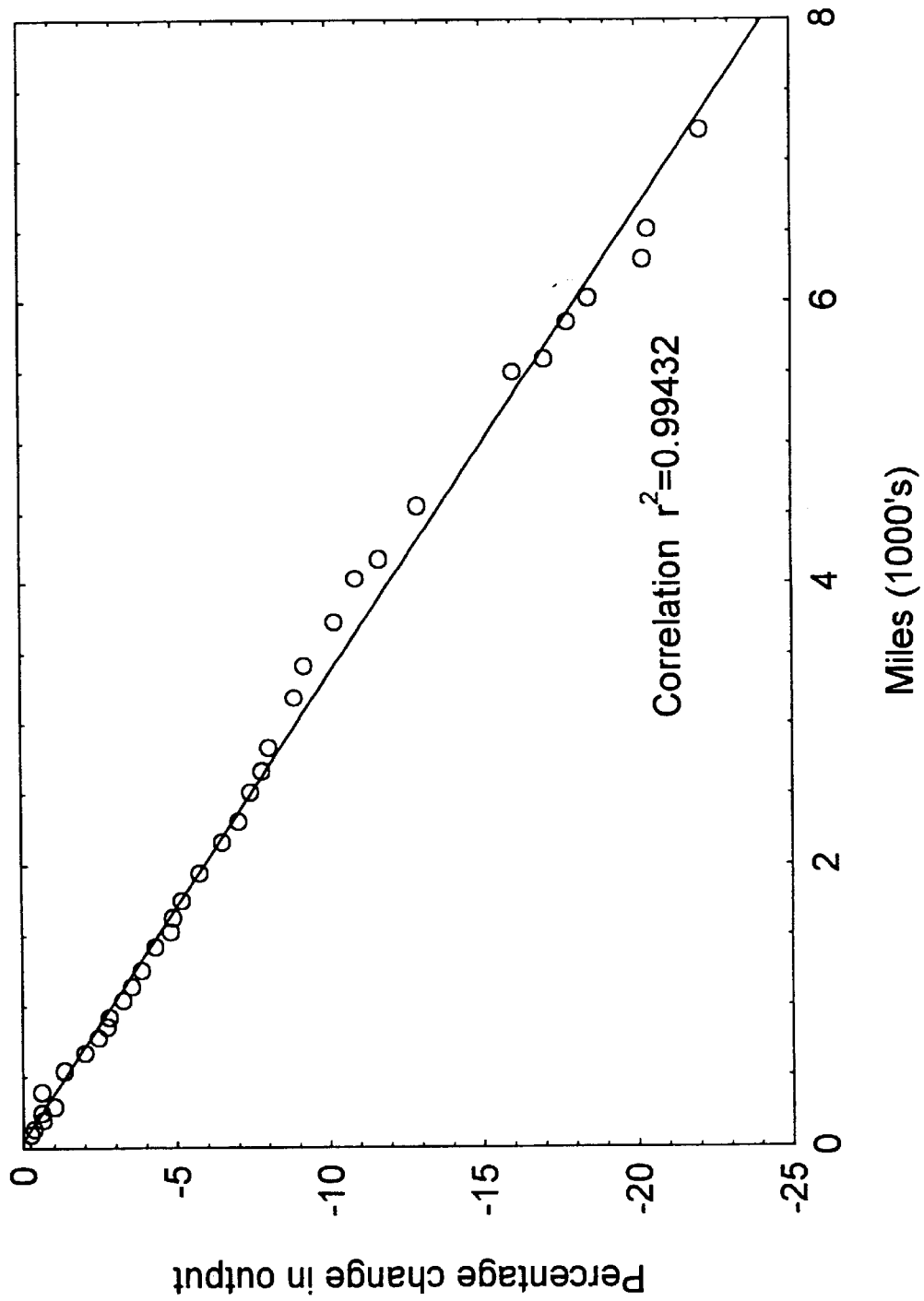
Figure 8:
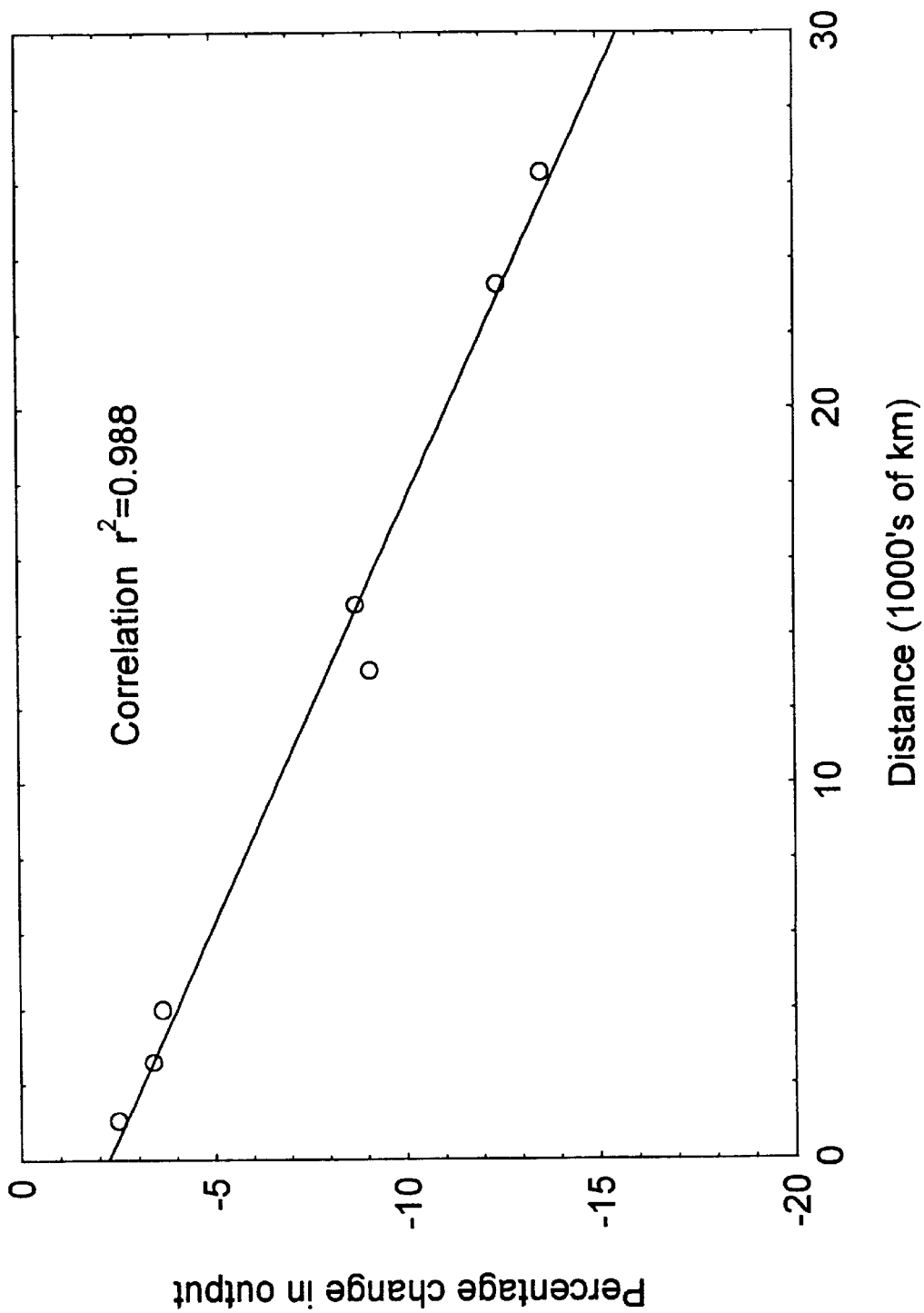

A preferred embodiment of the present invention will now be described, by way of example and with reference to the accompany drawings in which:

FIG. 1(a) shows the circuit diagram of a sensor head according to the invention, FIG. 1(b) shows the sensor head of FIG. 1(a) connected to measuring and display means, FIG. 2 shows a cross sectional view of the sensor head of FIG. 1(b), FIG. 3 shows the sensor head according to a second embodiment where the outer cylinder is replaced by an arrangement of conducting pins, FIG. 4(a) shows the sensor attached to an engine block, FIG. 4(b) shows the sensor alternatively attached to an engine sump, FIG. 5 shows the sensor attached to a secondary bypass filter of an engine, FIG. 6 shows a graph which plots the device output against soot concentration for a variety of oils from engines of different type, FIG. 7 shows a graph which plots the change in output against distance for a typical small petrol driven automobile, FIG. 8 shows a graph similar to FIG. 7 for a large diesel engined commercial vehicle, FIG. 9 shows a number of curves of sensor output against temperature for engine oils of different levels of contamination, FIG. 10 shows the variation in sensor output for different brands of engine oil, and FIG. 11 shows a typical plot of the real and imaginary part of permittivity for all frequencies.

PHYSICAL BASIS OF THE INVENTION

Mineral lubricating oil is an essentially non-polar liquid dielectric with very high resistivity that is to say, the passage of non alternating conduction current through it is negligible, even when loaded with conductive particles such as soot. It may be characterised by its permittivity, which is in general complex, consisting of a real and an imaginary part, that is $$\epsilon=\epsilon'-j\epsilon''$$

or equivalently, $$\epsilon=\epsilon'(1-j\,\text{Tan}\,\delta)$$

where $j=\sqrt{(-1)}$ and Tan $\delta=\epsilon''/\epsilon'$. The phase angle $\delta$ is a measure of the lossiness, or dissipation factor, of the dielectric, and will determine the maximum amplitude attainable by a tuned circuit of which it forms a part.

In any capacitor, the capacitance is always proportional to $\delta$, so capacitance is in general complex, and may be written as $$C=C_0(1-j\,\text{Tan}\,\delta)$$

where $C_0$ is the value of the capacitance with an otherwise lossless dielectric. It can be seen that the magnitude, Or modulus, of the capacitance is therefore $$|C|=C_0\sqrt{(1+\text{Tan}^2\delta)}$$

When the sensing element is a simple capacitor such as described, the idea of a lossy dielectric is intuitively clear, and the mathematical analysis is straightforward. However, the sensing element may also take the form of a short antenna radiating into the lossy dielectric medium, where the characteristics of the medium influence the loading on the antenna In this case the analysis, in which the near field components of the antenna are important, is more complicated, but the effect on the oscillator is the same, that is, the voltage and current will change with changes in the value of Tan $\delta$ of the medium. These changes may be measured and interpreted as changes in the quality of the oil. In an unused lubricating oil at a typical operating frequency, Tan $\delta$ is typically around 0.01, increasing to perhaps 0.1 for a heavily contaminated sample, while $\epsilon'$ is typically 2.25 to 2.45. For small concentrations of soot up to a few percent, Tan $\delta$ is approximately proportional to soot concentration, while the corresponding change in $\epsilon'$ is only a few percent at most. This means that Tan $\delta$ is the most suitable parameter for indicating oil quality, being insensitive to variations in the composition of clean oils, and having the greatest rate of change during use and subsequent contamination.

Apart from soot in engine oil, a further important contaminant is represented by oxidation products, which may also be present in hydraulic oils. Oxidation tends to occur in particular when the oil is hot, and is accelerated by the presence of catalytic agents such as copper, iron or water. These products consist generally of alcohols, aldehydes, and ketones, which will break down further into acids and esters in varying concentrations. Since these molecules tend to possess strong dipole moments, the oil becomes a more or less dilute solution of polar materials in a non polar solvent. Each polar molecule is associated with a particular relaxation time, or distribution of relaxation times, which are themselves dependent on temperature. As the, temperature increases, the viscosity falls, allowing greater dipole mobility and hence shorter relaxation times.

When $\epsilon''$ is plotted against $\epsilon'$ for all frequencies, that is from DC to several GHz, the resultant curve has the general shape shown in FIG. 11. An empirical model which usually fits the data is a modified form of the Cole Davidson equation:

$$(\epsilon-\epsilon_\infty)/(\epsilon_0-\epsilon_\infty)=(1+(j\omega\tau)^\alpha)^{-\beta}, 0<\alpha<1$$

where $\alpha$ and $\beta$ are both positive real numbers, and reflect the distributions of relaxation times $\tau$ of the many species present. When $\beta=1$ the curve forms an arc of a circle. The effect of $\alpha$ is to depress the centre of this circle below the imaginary axis, while the effect of $\beta$ is to skew the curve from a generally circular form. $\beta$ is usually quite close to 1. Examination of this expression shows that some care is required in selecting the operating frequency. Differentiation of the above expression shows that a low value of frequency $\omega$ will give rise to a rapid rate of change in Tan $\delta$, with frequency, making it unduly sensitive to the stability of the oscillator. At the peak value of Tan $\delta$ the rate of change of Tan $\delta$ with frequency is zero but this is true only for a particular oil at a particular temperature, making the device useless for all but a very limited range of conditions. At the higher frequencies, the rate of change is smaller, but so also is Tan $\delta$, so a tradeoff is necessary between sensitivity on the one hand and accuracy over a range of oils, temperatures and contaminants on the other. The small size of the device tends to dictate the use of higher frequencies, but these must not be so high as to require the use of unnecessarily costly components and construction techniques.

It can be shown that for small Tan $\delta$ the frequency is given approximately by $$\omega=\omega_0(1-\tfrac{1}{4}\text{Tan}^2\delta),$$

so a small change in Tan $\delta$ gives rise to a corresponding small change in $\omega$:

$$\Delta\omega=-\tfrac{1}{2}\omega_0 \text{Tan } \delta.\Delta(\text{Tan } \delta)$$

The relative change in frequency due to a change in Tan $\delta$ is therefore given by $$\Delta\omega/\omega=-\tfrac{1}{2}\text{Tan } \delta.\Delta(\text{Tan } \delta)$$

from which it can be seen that a small value of Tan $\delta$ (which is usually the case) will give rise to only a small change in frequency.

Determination of Tan $\delta$

The Tan $\delta$ term is sensed in any of a variety of ways, of which one is the measurement of the potential difference across a tuned circuit for example as shown in FIG. 1. It is well known that the impedance of a parallel LC or RLC circuit increases as the exciting frequency approaches the resonant frequency (for small Tan $\delta$ phase resonance and amplitude resonance are very nearly the same, the former being defined as the point at which the reactance, or imaginary part of the impedance, is zero, while the latter is the point at which the amplitude is a maximum), and that the potential, or voltage across the circuit increases in the same proportion. This apparent amplification is often referred to as the "Q" of the circuit, which is generally the ratio of reactance to resistance in an RLC circuit, but which in the context of a lossy dielectric is simply 1/Tan $\delta$.

If we assume for simplicity that the inductor in a tuned circuit possess no resistance, then the impedances of the inductor and capacitor are respectively.

$$Z_L=j\omega L$$

$$1/Z_C=j\omega C_0(1-j\text{ Tan }\delta)$$

where $\omega$ is the angular frequency of the current in the circuit. It can be shown that phase resonance occurs when the two impedances are equal, that is, when $$\omega_0^2=1/(LC_0)$$

At this frequency the magnitude of the impedance is given by $$|Z|=\sqrt{(L/C_0)}.1/\text{Tan }\delta$$

and it follows that the voltage across the circuit is inversely proportional to Tan $\delta$, all other losses being ignored. For small changes in Tan $\delta$ it can be shown that the percentage change in voltage is proportional to the percentage change in Tan $\delta$, that is $$\Delta V/V=-\Delta(\text{Tan }\delta)/\text{Tan }\delta$$

so that, owing to the negative sign in the above expression, an increase in Tan $\delta$ implies a corresponding decrease in voltage V. Note that by contrast with the corresponding analysis given above for the change in frequency with Tan $\delta$, the relative change in voltage is large for small values of Tan $\delta$. This provides good justification for the choice of amplitude, (rather than frequency), as the preferred measurand.

Given that the voltage across the tuned circuit changes, it follows that the current in the tuned circuit and associated, oscillator also changes. Since this change in current is a reflection of the change in oscillator voltage, it may then advantageously be used to indicate Tan $\delta$, and hence oil quality, as before. This arrangement allows the use of just two wires from the sensor, that is, one wire to supply power (from which the current is measured) and a second wire to provide the output from the temperature sensor. These two outputs may advantageously be duplexed, allowing the use of just one wire, with the sensor body providing the ground connection.

DESCRIPTION OF THE PREFERRED CIRCUIT

Referring to FIG 1(a), the sensing element/capacitor 1 of the sensor head H, has a capacitance between 1 pF and 50 pF, and is connected in parallel across inductor 2 (of High Q) via a short coaxial conductor 9. The AC voltage across the inductor 2 passes to the base of transistor 3 via series/coupling capacitor 4 which is provided to block the passage of DC current through the inductor 2. The transistor 3 is provided feedback elements such that the circuit is configured as, for example, a Colpitts oscillator. In this case, the series capacitor 4 and the feedback capacitors 5 and 6 appear across the sensing capacitor 1 to increase its value, so that the resonant frequency, which may be between 10 MHz and 300 MHz, is determined not only by the sensing capacitor but also to a lesser extent by capacitors 4, 5 and 6. The values of the bias resistors 7 and 8 are chosen to have only a small effect on the overall "Q" of the circuit. The output from the oscillator, which may be taken from the emitter of the transistor 3 to ensure a low impedance output, passes to a detector circuit 10 whose DC output is proportional to the amplitude of the signal at the base of the transistor, and is filtered to remove the high frequency component. The DC signal then passes to a low output impedance amplifier 11 which provides a small amount of gain and, more importantly, suitable buffering between the detector and the output lead.

In a further embodiment (not shown) the output from the sensor is simply the current drawn by the oscillator circuit, and is measured in the display means, which contains a stabilised constant voltage source. In a related embodiment the output from the temperature sensor is duplexed onto the power supply lead.

Optionally incorporated in the feedback loops of the amplifier are temperature sensitive elements such as diodes or thermistors which are used to maintain a more or less constant output for a given oil sample irrespective of temperature. In a preferred embodiment the sensor contains a temperature sensor 12 whose output passes directly to the display board and is read and interpreted in such a way as to apply temperature compensation by means of software. As shown in FIG 1a, the supplied voltage +V for the circuit is derived from a voltage regulator 13 which may also incorporate a temperature dependent element. The power input to the device, which may be 12V or 24V, is protected by surge suppressors against voltage spikes of up to 120 V such as may reasonably be expected on an automotive voltage supply. Both the power input terminal IN and the signal output terminal OUT incorporate EMC protection of EMC/RF filters 14a, 14b such that high frequency energy is not radiated by the device, nor is it affected by high frequency radiation from some external source.

FIG. 1b shows the sensor head H connected to a microprocessor 15 and display board 16, where the input to the microprocessor consists of a voltage TEMP dependent on temperature and the output voltage OUT from the sensor. The microprocessor includes a memory 17 and means for storage of data and calibration values, and also a lookup table for temperature compensation.

The Capacitive Sensor

The sensor, which is shown in cross section in FIG. 2, is in the form of a coaxial capacitor, typically 10 mm in diameter, and generously perforated with perforations or slots 30 in the outer cylinder 33 to allow the free passage of oil in the annular space between the cylinders 22, 33. In an alternative embodiment (not shown), the inner cylinder 22 can also have perforations. The flow of oil is at least approximately at right angles to the axis of the sensor. The outer cylinder 33, which is part of the metallic body 20 of the sensor H is at ground potential, and the size of the annular gap to the inner cylinder 22 is chosen so that the capacitance, including fringing effects, is approximately 1 pF to 50 pF. The inner, cylinder 22 extends backwards as a thin shaft or screw 24 into the body 20 of the sensor H, where it connects electrically with the printed circuit board (PCB) 23. The space between the PCB 23 and the sensing head is designed to prevent the ingress of oil from the engine into the PCB compartment, and incorporates elastomeric compression seals or "O" rings 31 and/or a bush 25 of insulating material such as PTFE (Polytetrafluoroethylene) or PEEK (Polyetheretherketone). External electrical connections are made by for example spade connectors or moulded automotive connectors 26.

The PCB 23 is held in place by retaining screws 32. The outer cylinder 33 is provided with a protective perforated screen or gauze. In an alternative embodiment, a protective gauze is not provided.

Since the wavelength at the. frequency of operation is generally much greater than the dimensions of the sensor, it is found that the effect of the perforations or slots is small, such that a high void ratio is possible.

In the annular region of a concentric capacitor, the electric field is essentially uniform, and is confined to the volume between the electrodes. Any change in the dielectric medium will be reflected by a corresponding change in the complex capacitance. If the outer earthed part of the capacitor is removed completely, the inner element will still radiate into the dielectric medium, and the impedance of this element, now behaving like an electrically short antenna, is dependent on its dimensions, the frequency of operation, and the electrical characteristics of the medium. It is therefore not essential for the sensing element to be in the form of a capacitor in which the field is totally contained, and it may simply take the form of a short stub. In constructing a derivative of the sensor for use in a test laboratory, it may be desirable for the sensing element to be as open as possible for ease of cleaning, but consistent with the need to keep radiated energy to a minimum and to allow the sensor to be insensitive to changes in the geometry and material of the vessel in which it is immersed. This requirement may be met by the provision of one or more grounded pins or elements in the vicinity of the active or live sensing element.

In a second embodiment, the sensing head differs in that the outer cylinder is replaced by an arrangement of vertical pins such that the alternating electromagnetic field around the central conductor links with the pins. FIG. 3 shows a view of this sensor with four grounded pins 50 in place of the coaxial outer conductor. It can be seen that the central conductor 52 is, in effect, a short antenna radiating into the dielectric medium. In a third embodiment, the sensing head (not shown) differs in that there is no grounded outer portion at all, this being provided by the engine block itself, or by the hardware (such as a sump, for example) into which the sensor is screwed. In this third embodiment the performance of the device would be dependent upon the precise geometry of the said hardware, and the frequency of operation is determined principally by the secondary coupling and feedback capacitors 4, 5 and 6.

In a further embodiment a metallic perforated screen or gauze is included to provide electromagnetic screening (and hence insensitivity to the sensor's immediate surroundings) and protection against mechanical damage.

The compartment 27 which contains the electronics is preferably cylindrical, being formed within a preferably hexagonal bar like a hexagonal nut to allow easy fitment to the engine or machine. It may be typically 30 mm across flats (A/F) and 18 mm deep, and may be fabricated for example from brass. As a protection against the ingress of dust and moisture, and as a protection against shock and vibration, the compartment 27 may be filled with a suitable potting compound such as silicone rubber or epoxy resin. As additional protection and to provide screening against internally or externally generated RF energy, a metallic conductive cap 28 is provided.

FIG. 4a shows one possible application of the preferred apparatus, in which the sensor H is attached directly to the pressurised oil supply port 62 of the engine 60. This oil supply port is usually near the primary oil filter 64, and an engine 60 usually has at least one tapped hole leading to the supply, frequently for the provision of an oil pressure switch or sender. The oil quality sensor can make advantageous use of one of these openings, given that an adaptor for the oil pressure switch or sender is provided such that both devices can operate simultaneously.

In an alternative application, a T-piece may be provided in the oil supply to, for example, an oil cooler or turbocharger, such that the sensor is exposed to the flow of oil.

FIG. 4b shows another possible application of the apparatus, in which it is attached to a sump 66 of the engine 60. In addition to the usual drain plug, large diesel engines are usually fitted with at least one other sump plug, such as may be used for a sump heater, for example. The apparatus fits into the sump in place of one of these other sump plugs.

These plugs are usually found on the side of the sump, so that an oil quality sensor H would lie essentially horizontally within the oil. Since there will always be constant motion of the oil due to the action of the oil pump, there will be no danger of oil stagnating within the sensor, which is generously provided with perforations or slots.

FIG. 5 shows an application of the apparatus in which it is attached directly to the inlet side of an oil bypass filter 68. The purpose of such a secondary filter is to remove particulate material down to 1 micron. In older or sooty engines in particular, such bypass filters tend to become clogged rapidly, and, since there is no other effective means of detecting this state, the oil quality sensor may therefore form part of the whole package, that is, bypass filter 68, oil quality sensor H, and associated fittings 70 and hardware (not shown).

FIG. 6 shows a scatter diagram of device output signal amplitude plotted against soot concentration. Several samples were taken from a wide variety of different sources, that is to say, there was a wide range of engine types, all using oils of different viscosities from different manufacturers. Although the sample size is relatively small, it can be seen that the correlation between soot content and sensor output amplitude is good, with a correlation coefficient of 91%. Soot concentration was obtained from a laboratory specialising in oil analysis, using standard techniques, for example reflectometry or gravimetric methods. It is seen from FIG. 6 that output amplitude is sensitive to soot content. It is also seen from FIG. 7 and FIG. 8 that output amplitude changes with distance (and hence with use) for both petrol and diesel engined vehicles.

What is claimed is:

1. Apparatus for measuring oil quality based on the permittivity (dielectrical coefficient) of the oil comprising a capacitive sensor for exposure to the oil, and an oscillator circuit including the sensor, characterised in that the oscillator circuit comprises one of a LC or crystal oscillator and provides an output signal, an amplitude of which is dependent upon a lossiness Tan δ of the oil, and a measuring device that responds to the amplitude of said output signal as a measure of oil quality.

2. Apparatus as claimed in claim 1, in which the oscillator circuit is such that it draws a current which changes with the lossiness Tan δ of the oil and gives a measure of oil quality.

3. Apparatus as claimed in claim 1, in which the amplitude is substantially inversely proportional to Tan δ.

4. Apparatus as claimed in claim 1, in which the sensor is incorporated in a sensor head adapted for fitting to one of an engine, machine filter or probe so as to be exposed to said oil.

5. Apparatus as claimed in claim 4, in which the oscillator circuit is incorporated in the sensor head.

6. Apparatus as claimed in claim 4, in which a temperature sensor is incorporated in the sensor head and produces a temperature output signal which is passed to the measuring means so as to allow temperature compensation in the output signal.

7. Apparatus as claimed in claim 6, in which the measuring means incorporates a processor and memory that incorporates a look-up table of temperature compensation values that are accessed by the processor according to the output signal and temperature output signal received by the processor.

8. Apparatus as claimed in claim 4, in which the sensor is mounted at the end of a long hollow flexible probe suitable for insertion into an orifice for testing oil.

9. Apparatus as claimed in claim 1, in which the measuring device includes a calibrator which is operable to cause a baseline value of the output signal to be saved in memory for reference in determining oil quality from subsequent values of the output signal.

10. Apparatus as claimed in claim 9, in which the memory is such as to retain stored values when power is disconnected.

11. Apparatus as claimed in claim 10, in which multiple sequential values based on the output signal are stored in the memory for subsequent downloading.

12. Apparatus as claimed in claim 1, in which the measuring device includes a display that displays an indication of oil quality.

13. Apparatus as claimed in claim 1, in which the output signal is suitable for interfacing with a data bus.

14. Apparatus as claimed in claim 1, in which the sensor comprises one or more capacitor plates pierced with openings to facilitate ingress of oil.

15. Apparatus as claimed in claim 14, comprising a pair of concentric capacitor plates.

16. Apparatus as claimed in claim 1, in which the sensor is intended to radiate into the oil dielectric medium like a short antenna or dielectric probe.

17. An oil bypass filter for attachment to an engine incorporating apparatus as claimed in claim 1.

18. A method of measuring oil quality based on the permittivity of the oil using an oscillator circuit including a capacitive sensor, characterised in that the sensor is one of a LC or crystal oscillator circuit and provides and output signal, an amplitude of which is dependent upon a lossiness Tan δ of the oil, and it is used to give a measure of oil quality.

* * * * *